United States Patent [19]

Neustadt et al.

[11] 4,163,053
[45] Jul. 31, 1979

[54] ANTI-HYPERTENSIVE 5-[2-(SUBSTITUTED ANILINOALKYLAMINO)-1-HYDROXYALKYL]SALICYLAMIDES

[75] Inventors: Bernard R. Neustadt; Elijah H. Gold, both of West Orange, N.J.

[73] Assignee: Schering Corporation, Kenilworth, N.J.

[21] Appl. No.: 864,983

[22] Filed: Dec. 27, 1977

[51] Int. Cl.² .................. C07C 103/26; C07C 143/75; A61K 31/165; A61K 31/18
[52] U.S. Cl. ............................. 424/230; 260/556 A; 260/556 AR; 260/556 S; 260/559 D; 260/559 S; 260/559 A; 424/321; 424/324
[58] Field of Search ........ 260/556 A, 556 AR, 556 S, 260/559 D, 559 S, 559 A; 424/321, 324, 230

[56] References Cited

U.S. PATENT DOCUMENTS

| | | | |
|---|---|---|---|
| 3,644,353 | 2/1972 | Lunts et al. | 260/559 S X |
| 3,676,493 | 7/1972 | Smith | 260/559 A |
| 3,723,524 | 3/1973 | Augstein et al. | 260/559 S |
| 3,816,516 | 6/1974 | Cox et al. | 260/559 S X |
| 3,888,898 | 6/1975 | Koppe et al. | 260/559 A X |
| 3,944,611 | 3/1976 | Smith | 260/559 A X |
| 3,959,369 | 5/1976 | Smith | 260/559 S X |
| 4,000,192 | 12/1976 | Lunts et al. | 260/559 S |
| 4,000,193 | 12/1976 | Lunts et al. | 260/559 S |
| 4,012,444 | 3/1977 | Lunts et al. | 260/559 S |
| 4,086,272 | 4/1978 | Cox et al. | 260/559 A X |

FOREIGN PATENT DOCUMENTS 1200886 8/1970 United Kingdom ................ 260/559 S

*Primary Examiner*—Thomas Waltz
*Attorney, Agent, or Firm*—Barbara L. Cowley Renda; Bruce M. Eisen

[57] ABSTRACT

5-[2-(Substituted-anilinoalkylamino)-1-hydroxyalkyl]-salicylamides, particularly useful as agents for the treatment of hypertension, are disclosed herein.

22 Claims, No Drawings

ANTI-HYPERTENSIVE 5-[2-(SUBSTITUTED ANILINOALKYLAMINO)-1-HYDROXYALKYL]-SALICYLAMIDES

The present invention is concerned with 5-[2-(substituted-anilinoalkylamino)-1-hydroxyalkyl]salicylamides. More particularly, this invention is concerned with compounds of the formula

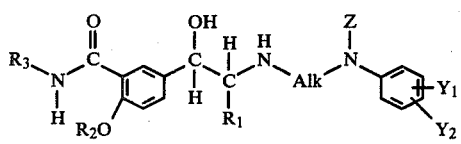

wherein $R_1$ is hydrogen or lower alkyl;
$R_2$ is hydrogen, lower alkyl, lower alkoxy(lower)alkyl, or hydroxy(lower)alkyl;
$R_3$ is hydrogen or lower alkyl;
Alk is an acyclic or cyclic alkylene bridge containing 2–10 carbon atoms, with the proviso that there are 2–6 carbon atoms separating the nitrogen atoms;
Z is hydrogen, lower alkyl, lower alkanoyl, lower alkylsulfonyl, arylsulfonyl, lower alkoxy(lower)alkyl or 2,2,2-trifluoroethyl;
$Y_1$ and $Y_2$ are independently hydrogen, halogen, hydroxy, trifluoromethyl, lower alkyl, lower alkoxy, nitro, amino, mono- or di- (lower)alkylamino, lower alkanoylamino, lower alkylsulfonyl amino, arylsulfonylamino, N-lower alkyl-N-lower alkanoylamino, or N-lower alkyl-N-lower alkylsulfonylamino; and the pharmaceutically acceptable acid addition salts thereof.

The lower alkyl groups referred to above contain 1–6 carbon atoms and are exemplified by methyl, ethyl, propyl, butyl, pentyl, hexyl and the corresponding branched chain isomers thereof. The lower alkoxy groups likewise contain 1–6 carbon atoms and are typified by methoxy, ethoxy, n-propoxy, isopropoxy, n-butoxy, sec.-butoxy, t-butoxy and the like.

The lower alkanoyl groups referred to above contain 1–6 carbon atoms and are typified by formyl, acetyl, butyryl, valeryl and the like.

The halogen atoms represented by $Y_1$ and $Y_2$ include fluorine, chlorine, bromine and iodine.

The alk bridges having 2–6 carbon atoms separating the nitrogen atoms are represented by acyclic groups such as ethylene, trimethylene, tetramethylene and pentametylene groups optionally substituted by lower alkyl groups. Thus, representative acyclic Alk groups of this invention are ethylene, 1-methylethylene, trimethylene or propylene, 1-methyltrimethylene, tetramethylene, 1-methyltetramethylene, 1,1-dimethyltrimethylene, 1,2-dimethyltrimethylene, 1-ethyltrimethylene, 1-methyl-2-ethyltetramethylene, pentamethylene, and 1,1-dimethyl-3-methylpentamethylene.

Certain of the compounds having the acyclic bridge may be represented by the formula

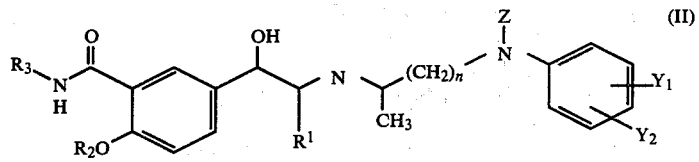

wherein n is 1–4, and $R_1$, $R_2$, $R_3$, Z, $Y_1$ and $Y_2$ are as hereinbefore defined. A particularly preferred bridge is of the formula

When the Alk bridge is cyclic the compounds of this invention may be represented by the formula

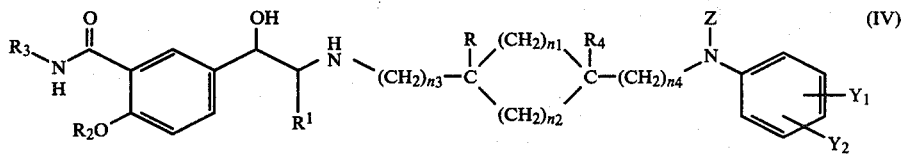

wherein
$n_1$ is 0–2,
$n_2$ is 1–5,
$n_1 + n_2$ is 2–6
$n_3$ and $n_4$ are independently 0 or 1,
R, $R_4$ and $R_5$ are independently hydrogen or lower alkyl with the proviso that the total number of carbon atoms in the Alk bridge does not exceed ten, and $R_1$, $R_2$, $R_3$, Z, $Y_1$ and $Y_2$ are as hereinbefore defined.

Where $n_3$ or $n_4$ is 0, it is to be understood that a carbon-nitrogen bond is indicated. Where $n_1$ is 0, it is understood that a carbon-carbon bond is indicated.

Cyclic Alk bridges may have lower alkyl substituents and include 1,2-cyclopentylene, 1,3-cyclopentylene, 1,2-cyclohexylene, 1,3-cyclohexylene, 1,4-cyclohexylene, 1-methyl-1,4-cyclohexylene, and 1,4-cycloheptylene. The cyclic bridges may also contain the cyclic group along with acyclic groups as represented by 1-cyclohexyl-4-methylene, 1-cyclopentyl-3-methylene, and 1-methylenecyclohexyl-4-methylene.

The pharmaceutically acceptable acid addition salts of the compounds of formula I may be derived from a variety of organic and inorganic acids, such as sulfuric, phosphoric, hydrochloric, hydrobromic, sulfamic, citric, lactic, oleoc, succinic, tartaric, cinnamic, acetic, benzoic, gluconic, ascorbic and related acids.

Within the scope of formula I there are certain preferential embodiments. $R_2$ and $R_3$ are preferably hydrogen. $R_1$ is preferably hydrogen or methyl.

Particularly preferred compounds of this invention are 5-(2-[3-(N-methylanilino)-2-propylamino]-1-hydroxyethyl)-salicylamide;

5-(2-[4-(N-methylanilino)-2-butylamino]-1-hydroxyethyl)-salicylamide;

5-(2-[5-(N-methylanilino)-2-pentylamino]-1-hydroxyethyl)-salicylamide;

5-(2-[4-(4,N-dimethylanilino)-2-butylamino]-1-hydroxyethyl)-salicylamide;

5-(2-[4-(4-fluoro-N-methylanilino)-2-butylamino]-1-hydroxyethyl)salicylamide; and 5-(2-[4-(4-chloro-N-methylanilino)-2-butylamino]-1-hydroxyethyl)salicylamide.

A method for the preparation of the compounds of formula I wherein $Y_1$ and $Y_2$ are other than nitro involves the reaction of a suitably protected anilinoalkyl amine of the formula

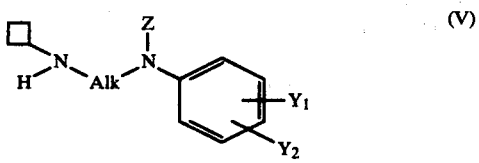

wherein Alk, Z, $Y_1$ and $Y_2$ are as hereinbefore defined except that $Y_1$ and $Y_2$ are other than nitro and □ is a suitable amino protecting group, with a compound of the formula

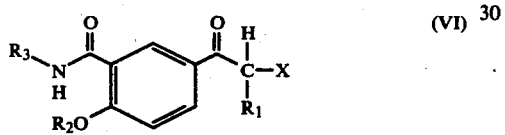

wherein X is chloro or bromo, in a suitable solvent in the presence of an acid acceptor to give a compound of the formula

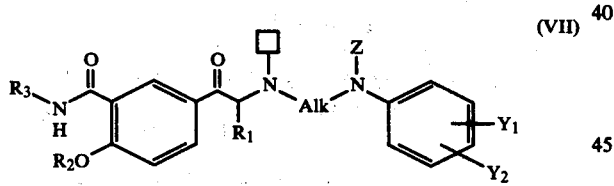

wherein □, $R_1$, $R_2$, $R_3$, Alk, Z, $Y_1$ and $Y_2$ are as hereinbefore defined except that $Y_1$ and $Y_2$ are other than nitro. The acid acceptor may be an organic base such as pyridine or triethylamine, or an inorganic base such as sodium or poassium carbonate.

The resultant compound of formula VII is then reduced to afford the corresponding hydroxy compound of the formula

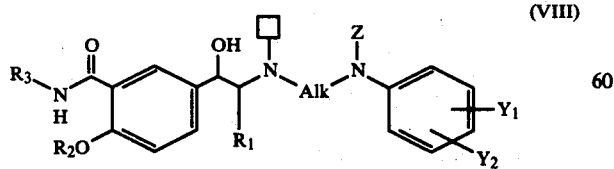

wherein □, $R_1$, $R_2$, $R_3$, Alk, Z, $Y_1$ and $Y_2$ are as hereinbefore defined except that $Y_1$ and $Y_2$ are other than nitro. A particularly suitable reducing agent for this process is sodium borohydride but other common ketone reducing agents such as lithium borohydride, potassium borohydride and hydrogen may also be utilized.

The blocking groups of the compound of the formula VIII wherein □, $R_1$, $R_2$, $R_3$, Alk, Z, $Y_1$ and $Y_2$ are as hereinbefore defined except that $Y_1$ and $Y_2$ are other than nitro, are then removed, typically by hydrogenation with a palladium-on-carbon or palladium catalyst in a lower alkanol such as methanol or ethanol.

In addition, the resultant compound of formula VII may be reduced directly to the desired product I by similar hydrogenation procedures.

In utilizing this process, if $R_2$ is hydrogen, the hydroxy group on the salicylamide portion of the molecule and the anilino functional group may be protected prior to the coupling reaction. This is typically and conveniently accomplished by utilizing the same blocking group utilized for the reactive amino functional group since it is then removed simultaneously in the last step of the process.

Suitable blocking groups for the protection of the amino and hydroxy groups are those conventionally used for this purpose such as benzyl, benzhydryl, trityl, carbobenzoxy and the like. The groups are then removed using hydrogenolysis to afford the desired final product.

Utilizing this process, the following compounds of this invention may be prepared:

5-(2-[4-(N-methylanilino)-2-(2-methyl)butylamino]-1-hydroxyethyl)salicylamide;

5-(2-[trans-4-(N-methylanilino)-1-cyclohexylamino]-1-hydroxyethyl)salicylamide;

5-(2-[cis-4-(N-methylanilino)-1-cyclohexylamino]-1-hydroxyethyl)salicylamide;

5-(2-[trans-4-(N,4-dimethylanilino)-1-cyclohexylamino]-1-hydroxyethyl)salicylamide;

5-[2-(trans-4-anilino-1-cyclohexylamino)-1-hydroxyethyl]-salicylamide;

5-(2-[trans-3-(N-methylanilino)-1-cyclohexylamino]-1-hydroxyethyl)salicylamide;

5-(2-[cis-3-(N-methylanilino)-1-cyclohexylamino]-1-hydroxyethyl)salicylamide;

5-(2-[trans-3-(N-methylanilino)-1-cyclopentylamino]-1-hydroxyethyl)salicylamide;

5-(2-[cis-3-(N-methylanilino)-1-cyclopentylamino]-1-hydroxyethyl)salicylamide;

5-(2-[trans-3-(N,4-dimethylanilino)-1-cyclopentylamino]-1-hydroxyethyl)salicylamide;

5-[2-(trans-3-anilino-1-cyclopentylamino)-1-hydroxyethyl]-salicylamide;

5-(2-[trans-3-(N-methylanilino)-1-cyclobutylamino]-1-hydroxyethyl)salicylamide;

5-(2-[cis-3-(N-methylanilino)-1-cyclobutylamino]-1-hydroxyethyl)salicylamide;

5-(2-[trans-3-(N,4-dimethylanilino)-1-cyclobutylamino]-1-hydroxyethyl)salicylamide;

5-[2-(trans-3-anilino-1-cyclobutylamino)-1-hydroxyethyl]-salicylamide;

5-(2-[trans-2-(N-methylanilino)-1-cyclopentylamino]-1-hydroxyethyl)salicylamide;

5-(2-[cis-2-(N-methylanilino)-1-cyclopentylamino]-1-hydroxyethyl)salicylamide;

5-(2-[cis-4-(N-methylanilino)-1-cycloheptylamino]-1-hydroxyethyl)salicylamide;

5-(2-[trans-4-(N-methylanilino)-1-cycloheptylamino]-1-hydroxyethyl)salicylamide;

5-(2-[trans-2-(N-methylanilino)-1-cyclohexylamino]-1-hydroxyethyl)salicylamide;

5-(2-[cis-2-(N-methylanilino)-1-cyclohexylamino]-1-hydroxyethyl)salicylamide;
5-(2-[trans-2-(N-methylanilino)-1-methyl-1-cyclohexylamino]-1-hydroxyethyl)salicylamide;
5-(2-[cis-2-(N-methylanilino)-1-methyl-1-cyclohexylamino]-1-hydroxyethyl)salicylamide;
5-(2-[trans-4-(4-fluoro-N-methylanilino)-1-cyclohexylamino]-1-hydroxyethyl)salicylamide;
5-(2-[cis-4-(4-fluoro-N-methylanilino)-1-cyclohexylamino]-1-hydroxyethyl)salicylamide;
5-(2-[trans-4-(4-trifluoromethyl-N-methylanilino)-1-cyclohexylamino]-1-hydroxyethyl)salicylamide;
5-(2-[cis-4-(4-trifluoromethyl-N-methylanilino)-1-cyclohexylamino]-1-hydroxyethyl)salicylamide;
5-(2-[trans-4-(N-acetylanilino)-1-cyclohexylamino]-1-hydroxyethyl)salicylamide;
5-(2-[cis-4-(N-acetylanilino)-1-cyclohexylamino]-1-hydroxyethyl)salicylamide;
5-(2-[trans-4-(N-ethylanilino)-1-cyclohexylamino]-1-hydroxyethyl)salicyclamide;
5-(2-[cis-4-(N-ethylanilino)-1-cyclohexylamino]-1-hydroxyethyl)salicylamide;
5-(2-[trans-4-(N-methanesulfonylanilino)-1-cyclohexylamino]-1-hydroxyethyl)salicylamide;
5-(2-[cis-4-(N-methanesulfonylanilino)-1-cyclohexylamino]-1-hydroxyethyl)salicyclamide;
5-(2-[cis-4-(N-methylanilino)methyl-1-cyclohexylamino]-1-hydroxyethyl)salicylamide;
5-(2-[trans-4-(N-methylanilino)methyl-1-cyclohexylamino]-1-hydroxyethyl)salicylamide;
5-(2-[cis-3-(N-methylanilino)methyl-1-cyclohexylamino]-1-hydroxyethyl)salicylamide;
5-(2-[trans-3-(N-methylanilino)methyl-1-cyclohexylamino]-1-hydroxyethyl)salicylamide;
5-(2-[cis-2-(N-methylanilino)methyl-1-cyclohexylamino]-1-hydroxyethyl)salicylamide;
5-(2-[trans-2-(N-methylanilino)methyl-1-cyclohexylamino]-1-hydroxyethyl)salicylamide;
5-(2-[cis-3-(N-methylanilino)methyl-1-cyclopentylamino]-1-hydroxyethyl)salicylamide;
5-(2-[trans-3-(N-methylanilino)methyl-1-cyclopentylamino]-1-hydroxyethyl)salicylamide;
5-(2-[cis-2-(N-methylanilino)methyl-1-cyclopentylamino]-1-hydroxyethyl)salicyclamide;
5-(2-[trans-2-(N-methylanilino)methyl-trans-2-(N-methylanilino)methyl-1-cyclopentylamino]-1-hydroxyethyl)salicyclamide;
5-(2-[cis-3-(N-methylanilino)methyl-1-cyclobutylamino]-1-hydroxyethyl)salicylamide;
5-(2-[trans-3-(N-methylanilino)methyl-1-cyclobutylamino]-1-hydroxyethyl)salicyclamide;
5-(2-[cis-4-(N-methylanilino)methyl-1-cycloheptylamino]-1-hydroxyethyl)salicylamide;
5-(2-[trans-4-(N-methylanilino)methyl-1-cycloheptylamino]-1-hydroxyethyl)salicylamide;
5-(2-[1-(cis-4-(N-methylanilino)methyl-1-cyclohexyl)ethylamino]-1-hydroxyethyl)salicylamide;
5-(2-[trans-4-(N-methylanilino)methyl-1-cyclohexyl)ethylamino]-1-hydroxyethyl)salicylamide;
5-(2-[1-(cis-3-(N-methylanilino)methyl-1-cyclohexyl)ethylamino]-1-hydroxyethyl)salicylamide;
5-(2-[1-(trans-3-(N-methylanilino)methyl-1-cyclohexyl)ethylamino]-1-hydroxyethyl)salicylamide;
5-(2-[1-(cis-2-(N-methylanilino)methyl-1-cyclohexyl)ethylamino]-1-hydroxyethyl)salicylamide;
5-(2-[1-(trans-2-(N-methylanilino)methyl-1-cyclohexyl)ethylamino]-1-hydroxyethyl)salicylamide;
5-(2-[1-(cis-3-(N-methylanilino)methyl-1-cyclopentyl)ethylamino]-1-hydroxyethyl)salicylamide;
5-(2-[1-(trans-3-(N-methylanilino)methyl-1-cyclopentyl)-ethylamino]-1-hydroxyethyl)salicylamide;
5-(2-[1-(cis-2-(N-methylanilino)methyl-1-cyclopentyl)ethylamino]-1-hydroxyethyl)salicylamide;
5-(2-[1-(trans-2-N-methylanilino)methyl-1-cyclopentyl)-ethylamino]-1-hydroxyethyl)salicylamide;
5-(2-[1-(cis-3-(N-methylanilino)methyl-1-cyclobutyl)ethylamino]-1-hydroxyethyl)salicylamide;
5-(2-[trans-1-(trans-3-(N-methylanilino)methyl-1-cyclobutyl)ethylamino]-1-hydroxyethyl)salicylamide;
5-(2-[1-(cis-4-(N-methylanilino)methyl-1-cycloheptyl)ethylamino]-1-hydroxyethyl)salicylamide;
5-(2-[1-(trans-4-(N-methylanilino)methyl-1-cycloheptyl)ethylamino]-1-hydroxyethyl)salicylamide;
5-(2-[1-(cis-4-(N-methylanilino)-1-cyclohexyl)ethylamino]-1-hydroxyethyl)salicylamide; and
5-(2-[1-(trans-4-(N-methylanilino)-1-cyclohexyl)ethylamino]-1-hydroxyethyl)salicylamide.

The compounds of formula II may be alternately prepared by reaction of a substituted anilinoketone of the formula

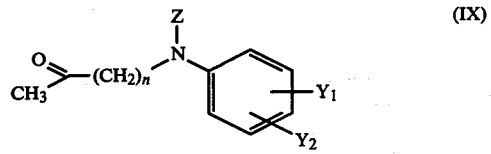

wherein Z, $Y_1$, $Y_2$ and n are as hereinbefore defined, with the appropriate salicylamide of the formula

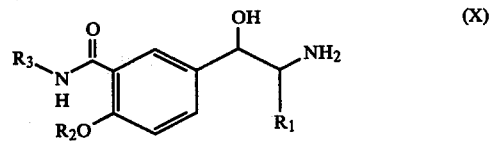

wherein $R_1$, $R_2$, and $R_3$ are as hereinbefore defined, in the presence of a reducing agent. The reaction is typically conducted in a solvent, lower alkanols such as methanol, ethanol, and propanol being preferred. Sodium borohydride and sodium cyanoborohydride are highly preferred reducing agents, but others, such as 9-BBN and lithium tetrahydrothexyllimonyl borohydride and catalytic hydrogenation, may also be utilized.

This is actually a preferred method for the preparation of the compounds of formula II.

Utilizing this process, the following compounds of this invention may be prepared:

5-(2-[4-(N-methylanilino)-2-butylamino]-1-hydroxyethyl)-salicylamide;
5-(2-[4-(4, N-dimethylanilino)-2-butylamino]-1-hydroxyethyl)-salicylamide;
5-(2-[4-(4-chloro-N-methylanilino)-2-butylamino]-1-hydroxyethyl)-salicylamide;
5-(2-[4-(3-chloro-4-methoxy-N-methylanilino)-2-butylamino]-1-hydroxyethyl)salicylamide;
5-(2-[4-(4-fluoro-N-methylanilino)-2-butylamino]-1-hydroxyethyl)-salicylamide;
5-(2-[4-(4-hydroxy-N-methylanilino)-2-butylamino]-1-hydroxyethyl)-salicylamide;
5-(2-[4-(4-methoxy-N-methylanilino)-2-butylamino]-1-hydroxyethyl)-salicylamide;

5-(2-[4-(4-nitro-N-methylanilino)-2-butylamino-]-1-hydroxyethyl)-salicylamide;

5-(2-[4-(4-amino-N-methylanilino)-2-butylamino]-1-hydroxyethyl)-salicylamide;

5-(2-[4-(4-acetamido-N-methylanilino)-2-butylamino]-1-hydroxyethyl)salicylamide;

5-(2-[4-(4-methylamino-N-methylanilino)-2-butylamino]-1-hydroxyethyl)salicylamide;

5-(2-[4-(4-methanesulfonamido-N-methylanilino)-2-butylamino]-1-hydroxyethyl)salicylamide;

5-(2-[4-(4-trifluoromethyl-N-methylanilino)-2-butylamino]-1-hydroxyethyl)salicylamide;

5-(2-[4-(3-trifluoromethyl-N-methylanilino)-2-butylamino]-1-hydroxyethyl)salicylamide;

5-(2-[4-(3-methoxy-N-methylanilino)-2-butylamino]-1-hydroxyethyl)-salicylamide;

5-(2-[4-(3-hydroxy-N-methylanilino)-2-butylamino]-1-hydroxyethyl)-salicylamide 5-(2-[4-(2,N-dimethylanilino)-2-butylamino]-1-hydroxyethyl)-salicylamide;

5-(2-[4-(2-chloro-N-methylanilino)-2-butylamino]-1-hydroxyethyl)-salicylamide;

5-(2-[4-(4-ethoxy-N-methylanilino)-2-butylamino]-1-hydroxyethyl)-salicylamide;

5-(2-[4-(4-isopropyl-N-methylanilino)-2-butylamino]-1-hydroxyethyl)salicylamide;

5-(2-[4-(N-methylanilino)-2-butylamino]-1-hydroxy-2-methylethyl)-salicylamide;

5-[2-(4-anilino-2-butylamino)-1-hydroxyethyl]-salicylamide;

5-(2-[4-(N-methanesulfonylanilino)-2-butylamino]-1-hydroxyethyl)-salicylamide;

5-(2-[4-(N-acetylanilino)-2-butylamino]-1-hydroxyethyl)-salicylamide;

5-(2-[4-(N-(2,2,2-trifluoroethyl)anilino)-2-butylamino]-1-hydroxyethyl)salicylamide;

5-(2-[4-(N-ethylanilino)-2-butylamino]-1-hydroxyethyl)salicylamide;

5-(2-[3-(N-methylanilino)-2-propylamino]-1-hydroxyethyl)-salicylamide;

5-(2-[3-(N,4-dimethylanilino)-2-propylamino]-1-hydroxyethyl)-salicylamide;

5-[2-(3-anilino-2-propylamino)-1-hydroxyethyl]-salicylamide;

5-(2-[5-(N-methylanilino)-2-pentylamino]-1-hydroxyethyl)-salicylamide;

5-(2-[5-(N,4-dimethylanilino)-2-pentylamino]-1-hydroxyethyl)-salicylamide;

5-[2-(5-anilino-2-pentylamino)-1-hydroxyethyl]-salicylamide;

5-(2-[6-(N-methylanilino)-2-hexylamino]-1-hydroxyethyl)-salicylamide;

5-(2-[6-(N,4-dimethylanilino)-2-hexylamino]-1-hydroxyethyl)-salicylamide;

5-[2-(6-anilino-2-hexylamino)-1-hydroxyethyl]-salicylamide;

5-(2-[4-(N-methylanilino)-2-(3-methyl)butylamino]-1-hydroxyethyl)-salicylamide;

5-(2-[4-(N-methylanilino)-2-pentylamino]-1-hydroxyethyl)-salicylamide;

5-(2-[3-(N-methylanilino)-2-butylamino]-1-hydroxyethyl)-salicylamide;

2-methoxy-5-(2-[4-(N-methylanilino)-2-butylamino]-1-hydroxyethyl)-benzamide;

2-(2-ethoxy)ethoxy-5-(2-[4-(N-methylanilino)-2-butylamino]-1-hydroxyethyl)benzamide;

2-(2-hydroxy)ethoxy-5-(2-[4-(N-methylanilino)-2-butylamino]-1-hydroxyethyl)benzamide;

5-(2-[4-(N-methylanilino)-2-butylamino]-1-hydroxyethyl)-N-methylsalicylamide; and 5-(2-[4-(N-methylanilino)-2-butylamino]-1-hydroxyethyl)-N-ethylsalicylamide.

The compounds of this invention are produced by the foregoing methods as stereoisomeric mixtures, i.e., they possess one or more asymmetric carbon atoms and therefore exist as chiral mixtures. The compounds may be used as their mixtures or separated into their enantiomeric and diastereomeric pure forms using conventional methods for the separation of such mixtures, such as fractional crystallization and chromatography. In addition, a desired diastereomer may be obtained utilizing pure chiral components.

The compounds of the present invention are useful in the treatment of cardiovascular disorders and particularly in the treatment of mammalian hypertension. Based on laboratory tests, it is considered that the effective dose ($ED_{50}$) by oral administration for a compound of the present invention will typically lie within the range of 0.05 to 10 mg/kg of mammalian weight.

The required daily dosage may be administered in single or divided doses. The exact dose to be administered will, of course, be dependent upon various factors such as the particular compound employed, age and weight of the subject mammal and the individual's response.

The compounds are preferably and most advantageously administered orally. The compounds may be combined with any suitable pharmaceutical carrier and administered in a variety of formulations such as tablets, capsules, syrups, elixirs or suspensions. The compounds may also be administered parenterally.

Typical acceptable pharmaceutical carriers for use in formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate, polyvinylpyrrolidone; polyvinyl alcohol; stearic acid; alkaline earth metal stearates such as magnesium stearate and calcium stearate; stearic acid vegetable oils such as peanut oil, cottonseed oil, sesame oil, olive oil and corn oil; non-ionic, cationic and anionic surfactants; ethylene glycol polymers; β-cyclodextrin; fatty alcohols; and hydrolyzed cereal solids; as well as other non-toxic compatible fillers, binders, disintegrants and lubricants commonly used in pharmaceutical formulations.

In treating certain patients with the compounds of this invention, it may be desirable to include other pharmaceutically active ingredients in the same dosage unit. For example, in treating patients in whom salt and water retention is a problem, effective amounts of conventional diuretics, e.g., hydrochlorothiazide or trichloromethiazide, may be included.

The following examples describe in detail compounds illustrative of the present invention and methods which have been devised for their preparation. It will be apparent to those skilled in the art that many modifications, both of materials and methods, may be practiced without departing from the purpose and intent of this disclosure.

EXAMPLE 1

5-(2-[4-(N-Methylanilino)-2-Butylamino]-1-Hydroxyethyl)Salicylamide

To a solution of 20 mmol 5-(2-amino-1-hydroxyethyl)salicylamide and 3.54 g (20 mmol) 4-(N-methylanilino)-2-butanone [procedure of Craig, et al, J. Org. Chem., 29, 410 (1964)] in 100 ml ethanol add 1.26 g (20 mmol) NaCNBH$_3$. Stir 16 hrs., concentrate, and partition between EtOAc and 1.0 N NaHCO$_3$ solution. Dry and concentrate the organic layer. Recrystallize the residue from methanol to give a white solid, mp 150°–2°.

EXAMPLE 2

5-(2-[3-(N-Methylanilino)-2-Propylamino]-1-Hydroxyethyl)Salicylamide

To To a solution of 20 mmol 5-(2-amino-hydroxyethyl)salicylamide and 3.26 g (20 mmol) N-methylanilino acetone in 100 ml methanol add 2.51 g (40 mmol) NaCNBH$_3$. Stir 16 hrs., concentrate, and partition between EtOAc and 1.0 N NaHCO$_3$ solution. Dry and concentrate the organic layer. Dissolve the foam in CHCl$_3$, and wash with water. Filter the solid which forms and recrystallize from EtOAc to give a white solid, mp 143°–5°.

EXAMPLE 3

5-(2-[5-(N-Methylanilino)-2-Pentylamino]-1-Hydroxyethyl)Salicylamide (a) 5-(N-Methylanilino)-2-Pentanone To 49.4 g (0.30 mol) 5-chloro-2-pentanone ethylene ketal and 64.2 g (0.60 mol) N-methylaniline in 100 ml toluene, add 27.7 g (0.33 mol) NaHCO$_3$ and 2.0 g KI. Reflux with a water separator overnight. Allow to cool, filter, and concentrate. Distill at 50°/0.1 mm to remove N-methylaniline. Stir the residual liquid with 175 ml 1.0 N HCl for 2 hrs. Neutralize with NaHCO$_3$ and extract with ether. Dry, concentrate, and distill to collect a fraction of b.p. 103°–110°/0.1 mm.

(b) 5-(2-[5-(N-Methylanilino)-2-Pentylamino]-1-Hydroxyethyl)Salicylamide

Combine the above ketone (4.3 g=21 mmol) with 20 mmol 5-(2-amino-1-hydroxyethyl)salicylamide and 2.0 g 10% Pd/C in 200 ml methanol. Hydrogenate at 60 psi for 20 hrs. Filter the catalyst, concentrate, and partition the residue between EtOAc and 1.0 N NaHCO$_3$ solution. The organic layer deposits a solid. Filter and recrystallize from methanol to give a white solid, mp 155°–7°.

EXAMPLE 4

5-(2-[4-(4-Chloro-N-Methylanilino)-2-Butylamino]-1-Hydroxyethyl)Salicylamide To a solution of 20 mmol 5-(2-amino-1-hydroxyethyl)salicylamide and 4.22 g (20 mmol) 4-(4-chloro-N-methylanilino)-2-butanone [mp 60°–1°, prepared by procedure of Craig, et al, J. Org. Chem., 29, 410 (1964)] in 100 ml methanol add 2.52 g (40 mmol) NaCNBH$_3$. Stir 6 days, concentrate, and partition between EtOAc and 1.0 N NaHCO$_3$ solution. Wash the organic layer with 1.0 N HCl. Neutralize the aqueous portion with NaHCO$_3$ and extract with EtOAc. Dry, concentrate, and recrystallize the residue from EtOAc-hexane to give a white solid, mp 127°–9°.

EXAMPLE 5

5-(2-[-4-(4,N-Dimethylanilino)-2-Butylamino]-1-Hydroxyethyl)Salicylamide

To a solution of 20 mmol 5-(2-amino-1-hydroxyethyl)salicylamide and 5.7 g (30 mmol) 4-(N,4-dimethylanilino)-2-butanone [b.p. 93°–6°/0.1 mm, prepared by procedure of Craig, et al, J. Org. Chem., 29, 410 (1964)] in 150 ml methanol, add 1.9 g (30 mmol) NaCNBH$_3$. After 20 hrs., concentrate, and partition between EtOAc and 1.0 N NaHCO$_3$ solution. Dry and concentrate. Warm the foam with EtOAc to give a white solid, m.p. 123°–6°.

EXAMPLE 6

5-(2-[6-(N-Methylanilino)-2-Hexylamino]-1-hydroxyethyl)-Salicylamide (a) 2-Benzyloxy-5-(2-[Benzyl-6-(N-Methylanilino)-2-Hexylamino]-1-Hydroxyethyl)Benzamide To N-(5-benzylaminohexyl)-N-methylaniline (3.06 g=10 mmol) and 3.48 g (10 mmol) 2-benzyloxy-5-(bromoacetyl)benzamide in 35 ml dimethylformamide, add 2.70 g (20 mmol) K$_2$CO$_3$. Stir 20 hrs. and pour into 150 ml water. Allow the gum to settle, decant, and dissolve the gum in ether. Extract with 1.0 N HCl, and then neutralize into NaHCO$_3$ and extract with EtOAc. Dry, concentrate, and dissolve the oil in 50 ml ethanol. Add 0.3 g (8 mmol) NaBH$_4$, stir 20 hrs., and concentrate. Partition between EtOAc and 1.0 N NaHCO$_3$. Dry and concentrate to give a yellow foam.

(b) 5-(2-[6-(N-Methylanilino)-2-Hexylamino]-1-Hydroxyethyl)Salicylamide

Add the above amine to 250 ml ethanol containing 1.0 g 5% Pd/C. Hydrogenate at 60 psi for 20 hrs., filter and concentrate. Recrystallize the tacky solid from methanol to give a white solid, mp 157°–60°.

What is claimed is:

1. A compound of the formula

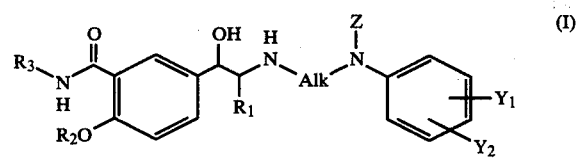

wherein
- R$_1$ is hydrogen or lower alkyl;
- R$_2$ is hydrogen, lower alkyl, lower alkoxy(lower)alkyl, or hydroxy(lower)alkyl;
- R$_3$ is hydrogen or lower alkyl;
- Alk is an acyclic or cyclic alkylene bridge containing 2–10 carbon atoms, with the proviso that there are 2–6 carbon atoms separating the nitrogen atoms;
- Z is hydrogen, lower alkyl, lower alkanoyl, lower alkylsulfonyl, arylsulfonyl, lower alkoxy(lower)alkyl or 2,2,2-trifluoroethyl;
- Y$_1$ and Y$_2$ are independently hydrogen, halogen, hydroxy, trifluoromethyl, lower alkyl, lower alkoxy, nitro, amino, mono- or di- (lower)alkylamino, lower alkanoylamino, lower alkylsulfonylamino, arylsulfonylamino, N-lower alkyl-N-lower alkanoylamino, or N-lower alkyl-N-lower alkylsulfonylamino; and the pharmaceutically acceptable acid addition salts thereof.

2. A compound according to claim 1 wherein the Alk bridge is an acyclic alkylene group.

3. A compound according to claim 2 wherein the Alk bridge is of the formula

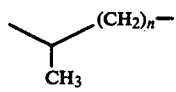

wherein n is 1–4.

4. A compound according to claim 1 wherein the Alk bridge is of the formula

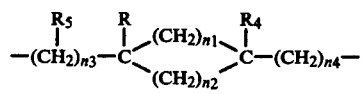

wherein $n_1$ is 0–2, $n_2$ is 1–5, $n_1+n_2$ is 2–6, $n_3$ and $n_4$ are independently 0 or 1, R, $R_4$ and $R_5$ are independently hydrogen or lower alkyl with the proviso that the total number of carbon atoms in the bridge does not exceed ten.

5. A compound according to claim 3 wherein the bridge is an alkylene group of the formula

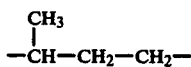

6. A compound according to claim 3 which is 5-(2-[3-N-methylanilino)-2-propylamino]-1-hydroxyethyl)-salicylamide.

7. A compound according to claim 3 which is 5-(2-[5-(N-methylanilino)-2-pentylamino]-1-hydroxyethyl)-salicylamide.

8. A compound according to claim 5 which is 5-(2-[4-(N-methylanilino)-2-butylamino]-1-hydroxyethyl)-salicylamide.

9. A compound according to claim 5 which is 5-(2-[4,N-dimethylanilino)-2-butylamino]-1-hydroxyethyl)-salicylamide.

10. A compound according to claim 5 which is 5-(2-[4-(4-chloro-N-methylanilino)-2-butylamino]-1-hydroxyethyl)salicylamide.

11. A compound according to claim 5 which is 5-(2-[4-(4-fluoro-N-methylanilino)-2-butylamino]-1-hydroxyethyl)salicylamide.

12. A pharmaceutical composition useful in the treatment of hypertension containing an antihypertensive amount of a compound of claim 1 together with a pharmaceutical carrier therefor.

13. A composition according to claim 12 which comprises 5-(2-[4-(N-methylanilino)-2-butylamino]-1-hydroxyethyl)salicylamide.

14. A composition according to claim 12 which comprises 5-(2-[4,N-dimethylanilino)-2-butylamino]-1-hydroxyethyl)salicylamide.

15. A composition according to claim 12 which comprises 5-(2-[4-(4-chloro-N-methylanilino)-2-butylamino]-1-hydroxyethyl)salicylamide.

16. A composition according to claim 12 which comprises 5-(2-[4-(4-fluoro-N-methylanilino)-2-butylamino]-1-hydroxyethyl)salicylamide.

17. A method of effecting an antihypertensive response in a mammal in need of such therapy which comprises administering to said mammal a composition of claim 12.

18. A method according to claim 17 which comprises administering 5-(2-[4-(N-methylanilino)-2-butylamino]-1-hydroxyethyl)salicylamide.

19. A method according to claim 17 which comprises administering 5-(2-[4-(4,N-dimethylanilino)-2-butylamino]-1-hydroxyethyl)salicylamide.

20. A method according to claim 17 which comprises administering 5-(2-[4-(4-chloro-N-methylanilino)-2-butylamino]-1-hydroxyethyl)salicylamide.

21. A method according to claim 17 which comprises administering 5-(2-[4-(4-fluoro-N-methylanilino)-2-butylamino]-1-hydroxyethyl)salicylamide.

22. A method according to claim 17 wherein the method of administration is oral.

* * * * *

UNITED STATES PATENT AND TRADEMARK OFFICE
CERTIFICATE OF CORRECTION

PATENT NO. : 4,163,053
DATED : July 31, 1979
INVENTOR(S) : Bernard R. Neustadt and Elijah H. Gold It is certified that error appears in the above-identified patent and that said Letters Patent are hereby corrected as shown below:

Column 1, line 67, "tametylene" should read --tamethylene--;

In formula II:

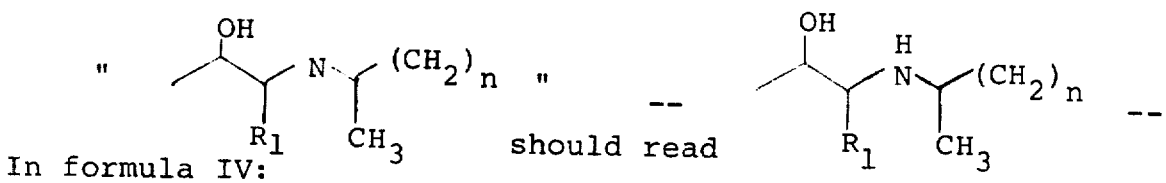

In formula IV:

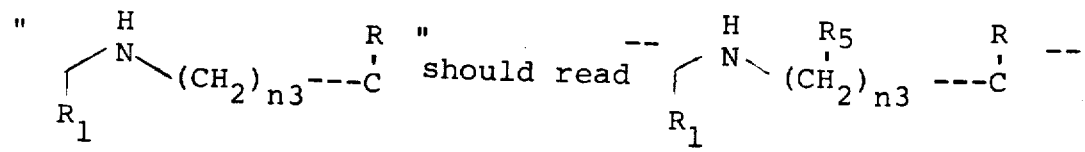

column 2, line 62, "oleoc" should read --oleic--; column 3, line 52, "poassium" should read --potassium--; column 5, line 20, "salicyclamide" should read --salicylamide--; column 5, line 26, "salicyclamide" should read --salicylamide--; column 5, line 44, "salicyclamide" should read --salicylamide--; column 5, lines 45-6, "(N-methylanilino)methyl-trans-2-(N-methylanilino)methyl-1-cyclopentylamino" should read --(N-methylanilino)methyl-1-cyclopentylamino--; column 5, line 47, "salicyclamide" should

UNITED STATES PATENT AND TRADEMARK OFFICE
CERTIFICATE OF CORRECTION

PATENT NO. : 4,163,053
DATED : July 31, 1979
INVENTOR(S) : Bernard R. Neustadt and Elijah H. Gold It is certified that error appears in the above-identified patent and that said Letters Patent are hereby corrected as shown below:

read --salicylamide--; column 5, line 51, "salicyclamide" should read --salicylamide--; column 5, line 58, "5-(2-/ trans-4-(N-" should read --5-(2-/ 1-(trans-4-(N---;  column 6, line 11, "5-(2-/ trans-1-(trans" should read --5-(2-/ 1-(trans--; column 6, line 56, "5-(2-/ 4-(4,   N-dimethylanilino)" should read --5-(2-/ 4-(4,N-dimethylanilino)--;

column 9, line 19, "To To a solution" should read --To a solution--; column 9, line 19, "mmol 5-(2-amino-hydroxye-" should read -- mmol 5-(2-amino-1-hydroxye---.

Signed and Sealed this

Twenty-ninth Day of April 1980

[SEAL]

Attest:

SIDNEY A. DIAMOND

Attesting Officer    Commissioner of Patents and Trademarks